US012485046B2

(12) United States Patent
Aochi

(10) Patent No.: US 12,485,046 B2
(45) Date of Patent: Dec. 2, 2025

(54) TAPE-TYPE DISPOSABLE DIAPER

(71) Applicant: DAIO PAPER CORPORATION, Ehime (JP)

(72) Inventor: Kohei Aochi, Tochigi (JP)

(73) Assignee: Daio Paper Corporation, Ehime (JP)

(*) Notice: Subject to any disclaimer, the term of this patent is extended or adjusted under 35 U.S.C. 154(b) by 229 days.

(21) Appl. No.: 18/265,140

(22) PCT Filed: Jan. 26, 2022

(86) PCT No.: PCT/JP2022/002763
§ 371 (c)(1),
(2) Date: Jun. 2, 2023

(87) PCT Pub. No.: WO2022/185790
PCT Pub. Date: Sep. 9, 2022

(65) Prior Publication Data

US 2024/0108518 A1 Apr. 4, 2024

(30) Foreign Application Priority Data

Mar. 3, 2021 (JP) ................................ 2021-033331

(51) Int. Cl.
*A61F 13/56* (2006.01)
*A61F 13/49* (2006.01)

(52) U.S. Cl.
CPC .... *A61F 13/5644* (2013.01); *A61F 13/49012* (2013.01); *A61F 13/49017* (2013.01)

(58) Field of Classification Search
CPC .......... A61F 13/49012; A61F 13/49017; A61F 13/56; A61F 13/5633; A61F 13/49007; A61F 13/5644
See application file for complete search history.

(56) References Cited

U.S. PATENT DOCUMENTS

2007/0129700 A1 6/2007 Yoshida
2010/0249744 A1* 9/2010 Akiyama .............. A61F 13/622 604/391
(Continued)

FOREIGN PATENT DOCUMENTS

CN 115414187 A * 12/2022 ............ A61F 13/58
JP 1993-039523 U 5/1993
(Continued)

OTHER PUBLICATIONS

Extended European Search Report for EP Application No. 22762849.2, dated Nov. 8, 2024.
(Continued)

*Primary Examiner* — Susan S Su
(74) *Attorney, Agent, or Firm* — Andrus Intellectual Property Law, LLP

(57) ABSTRACT

A tape-type disposable diaper having upper and lower fastening tapes divided by a perforated line, wherein the initial point of the perforated line is noticeable. The diaper has a fastening tape extending widthwise from each of the opposed lateral portions of the dorsal region, wherein, assuming that a part of the side edge of each fastening tape located between the fastening parts of the waist-side flap and the round-leg-side flap is equally divided in the front-back direction into the first edge located closer to the waist, the second edge located closer to the round-leg area, and the third edge located therebetween, at least part of the third edge is provided with a notch dented proximally from the first and second edges. By noticing the notch, the user recognizes the perforated line extending proximally from the notch, and tears along the perforated line for wearing the diaper.

4 Claims, 12 Drawing Sheets

(56) References Cited

U.S. PATENT DOCUMENTS

| | | | | |
|---|---|---|---|---|
| 2011/0301563 | A1* | 12/2011 | Maruhata ................ | A61F 13/58 604/389 |
| 2012/0289924 | A1* | 11/2012 | Nishida ................. | A61F 13/622 604/389 |

FOREIGN PATENT DOCUMENTS

| | | | |
|---|---|---|---|
| JP | 2005160506 | A | 6/2005 |
| JP | 2007-014639 | | 1/2007 |
| JP | 2011-147496 | | 8/2011 |
| JP | 2011-200336 | | 10/2011 |
| JP | 2014-028064 | | 2/2014 |
| JP | 6087081 | | 2/2014 |
| JP | 2014068849 | A | 4/2014 |
| JP | 2014-104312 | | 6/2014 |
| JP | 6440471 | | 12/2018 |

OTHER PUBLICATIONS

International Search Report and the Written Opinion for PCT/JP2022/002763, dated Apr. 19, 2022.

* cited by examiner

[FIG.1]
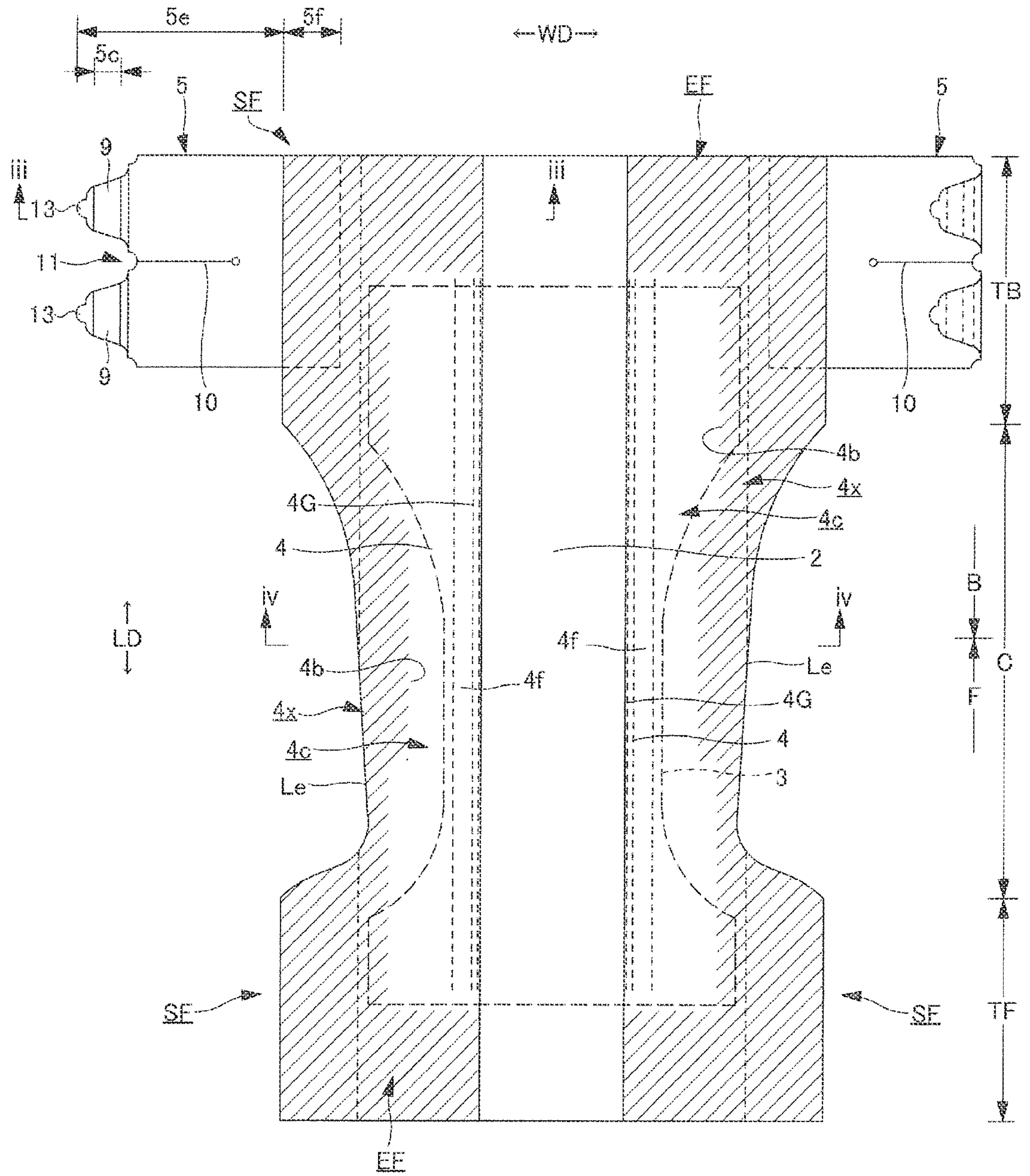

[FIG.2]
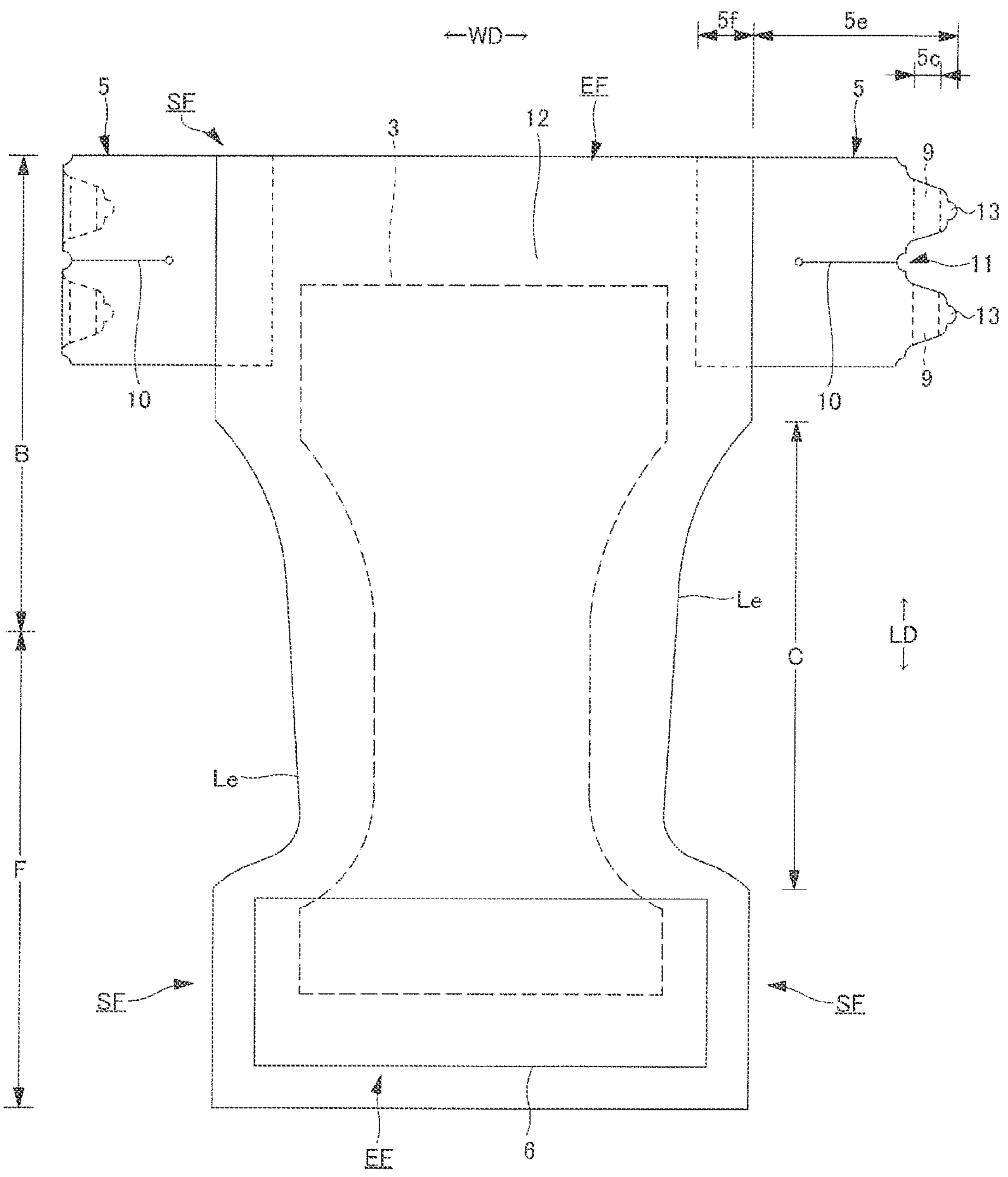

[FIG.3]
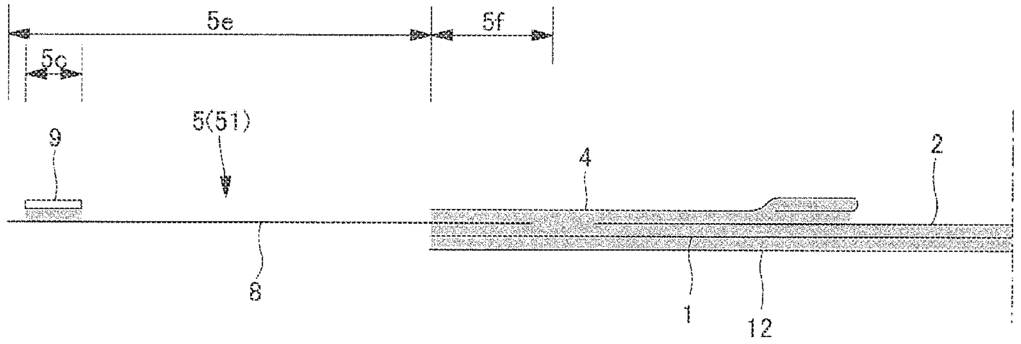

[FIG.4]
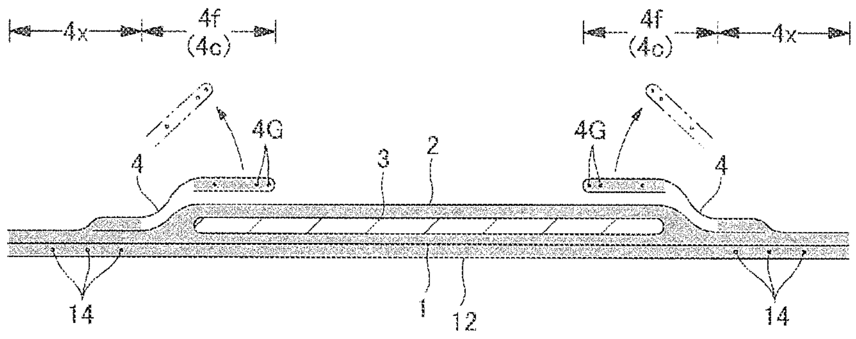

[FIG.5]
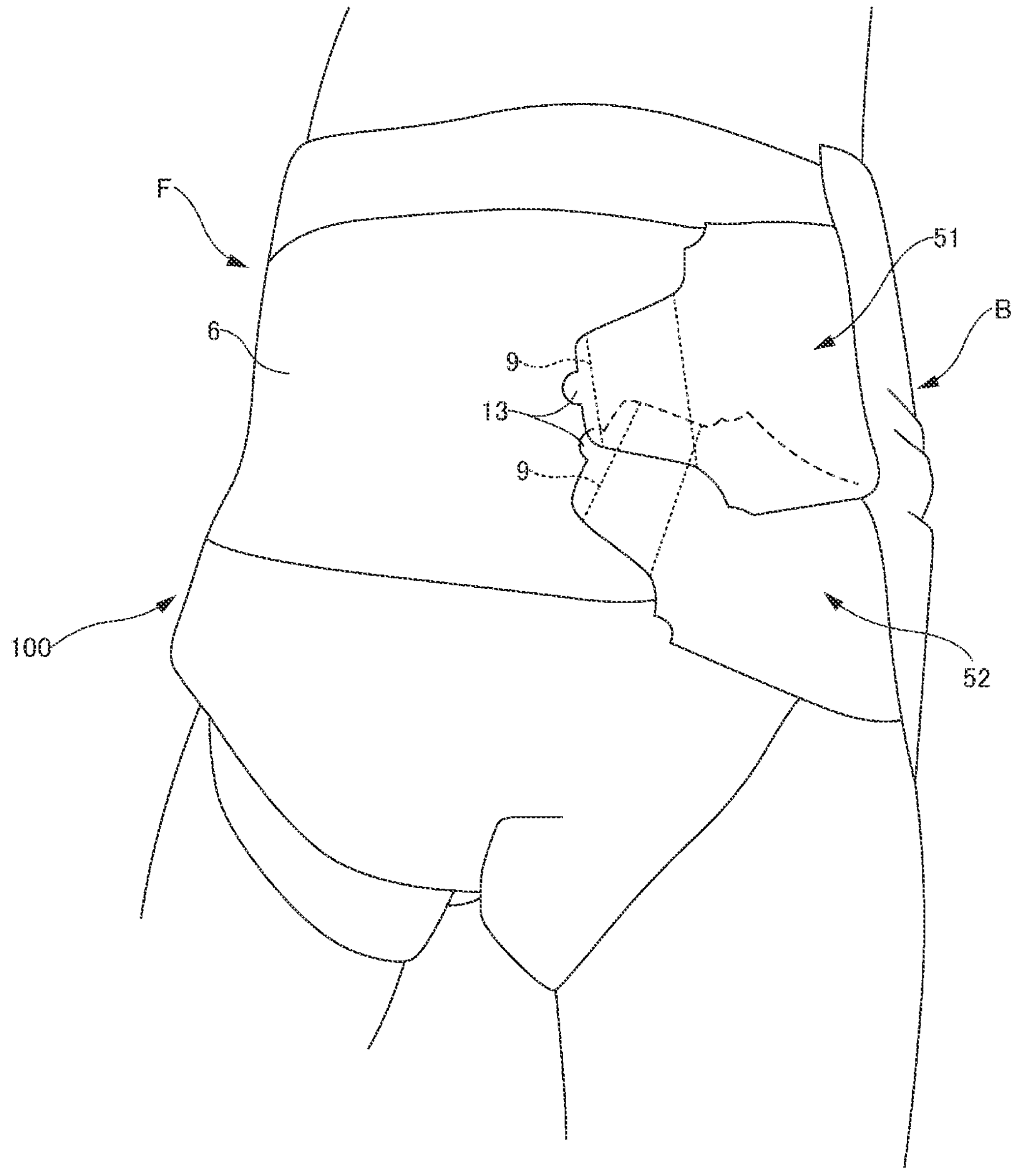

[FIG.6]
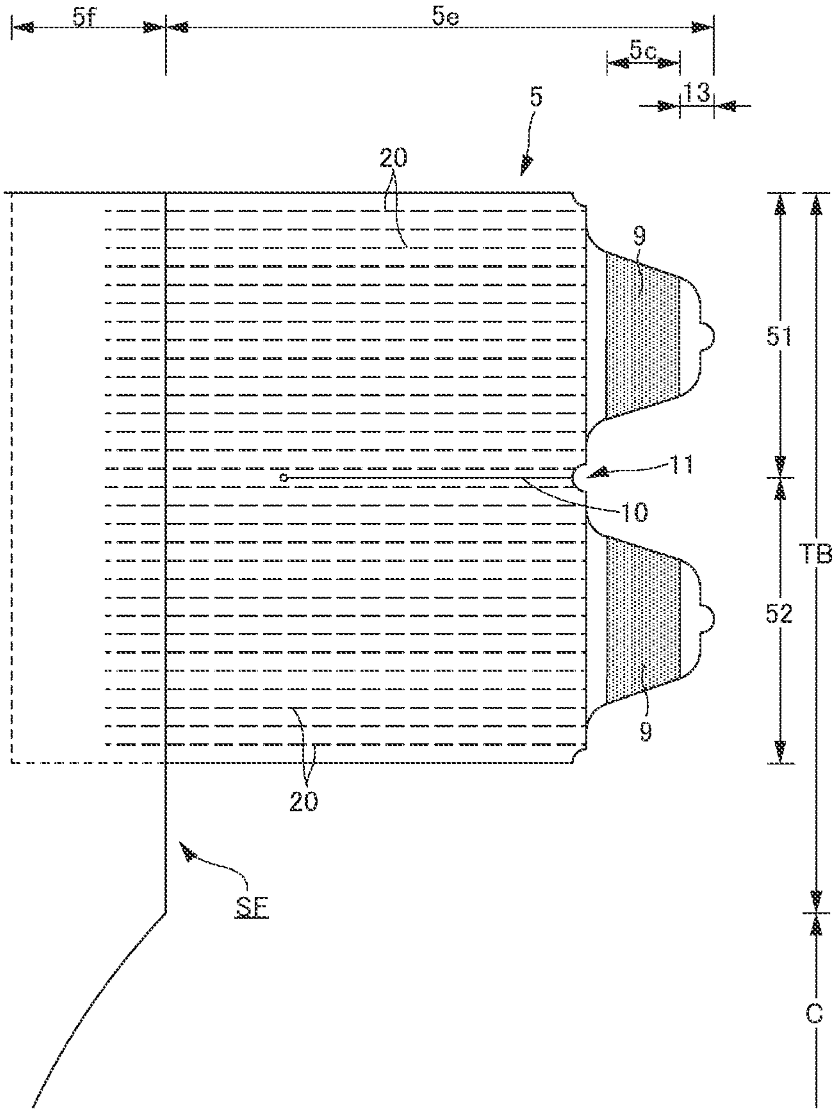

[FIG.7]
(a)
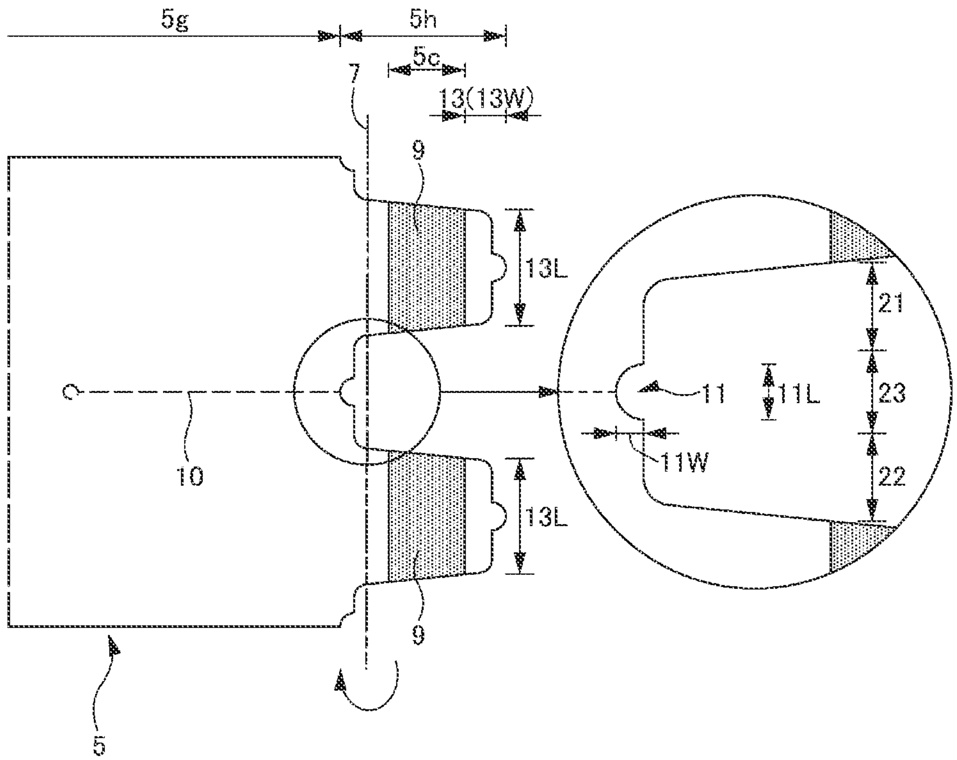
(b)
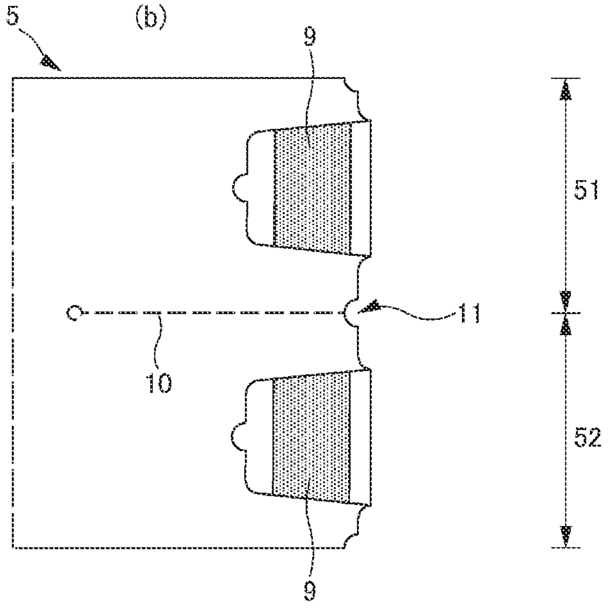

[FIG.8]
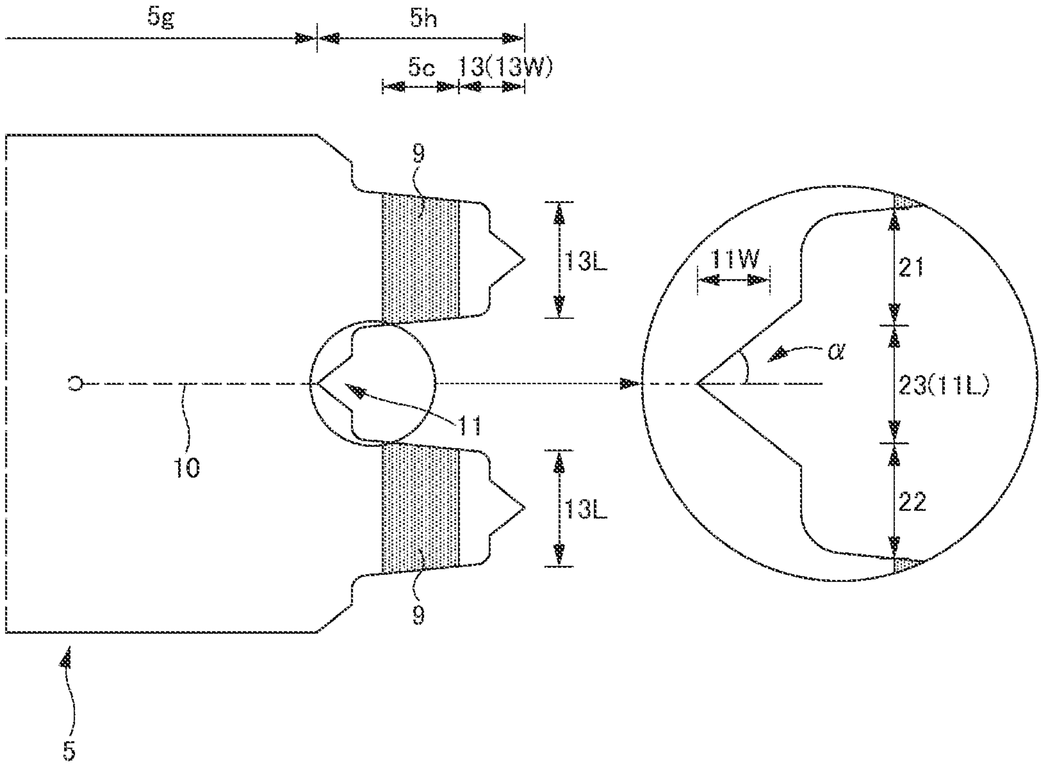

[FIG.9]
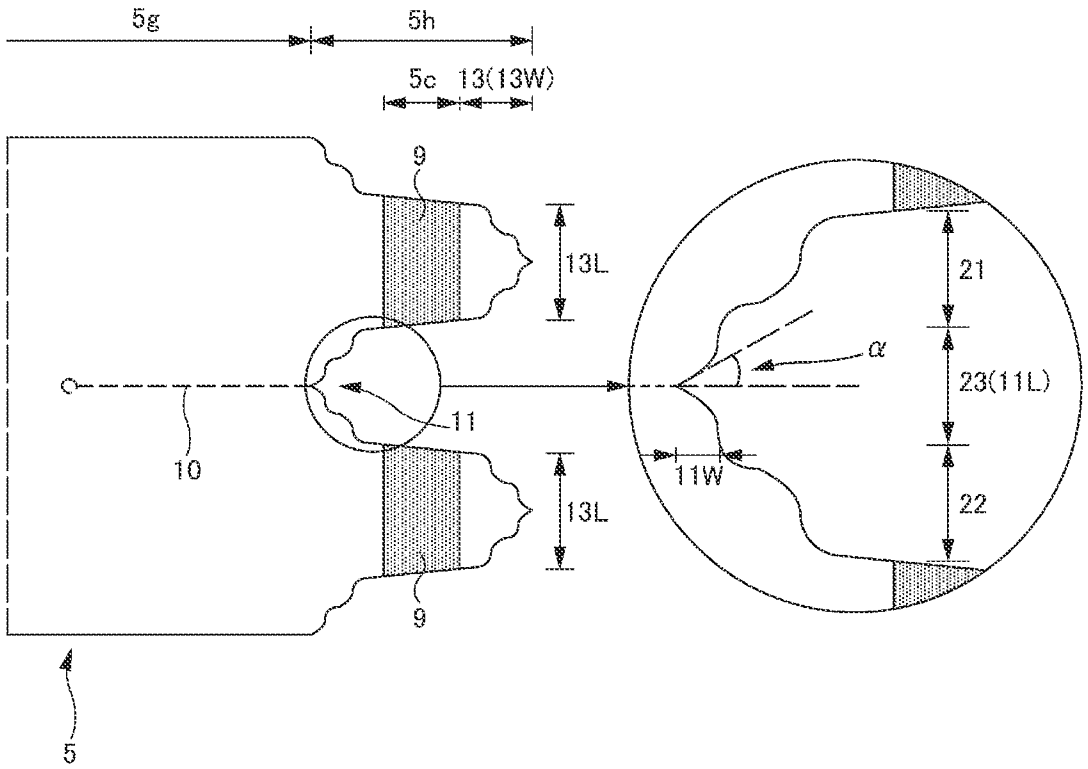

[FIG.10]
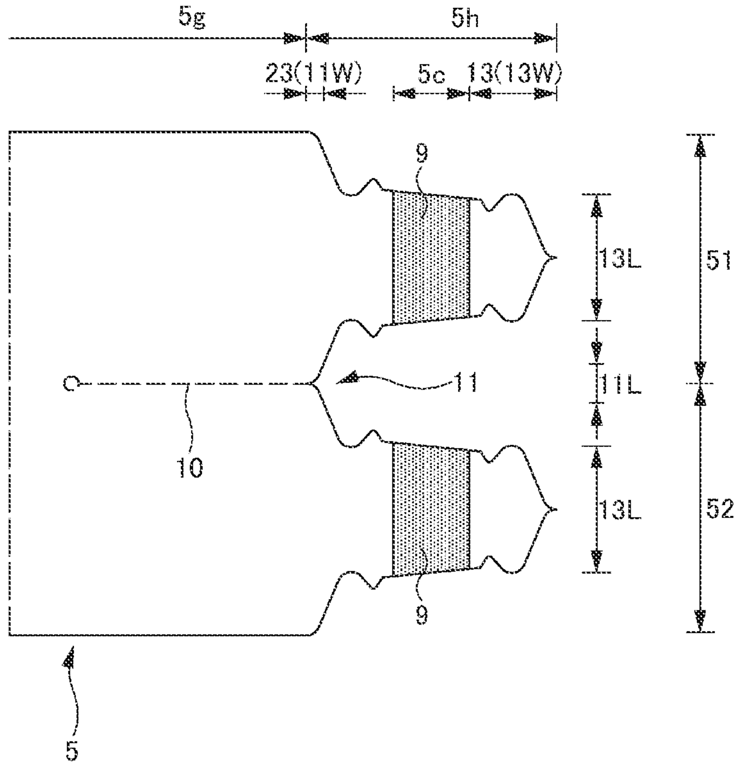

[FIG.11]
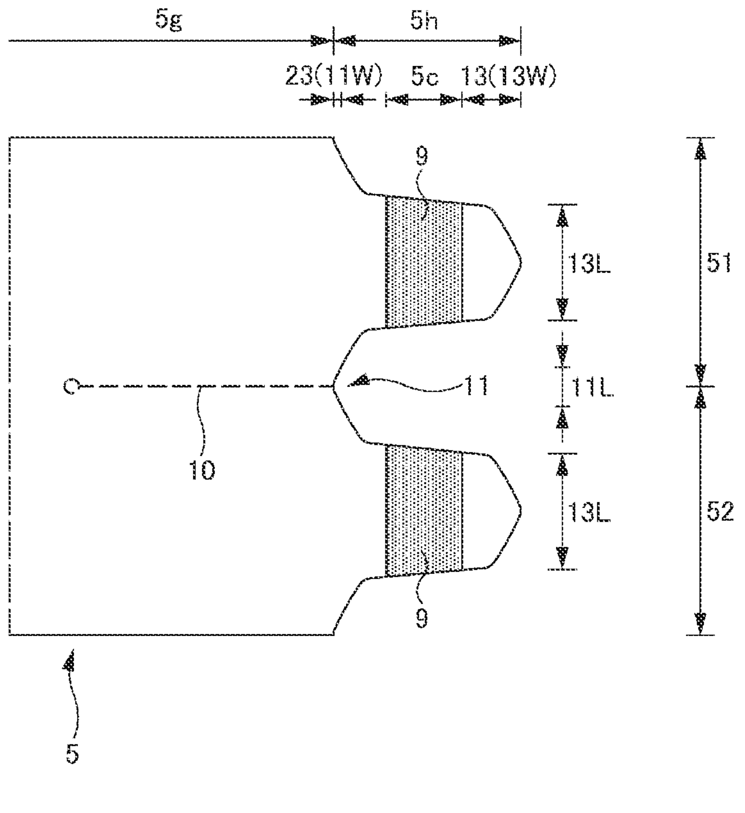

[FIG.12]
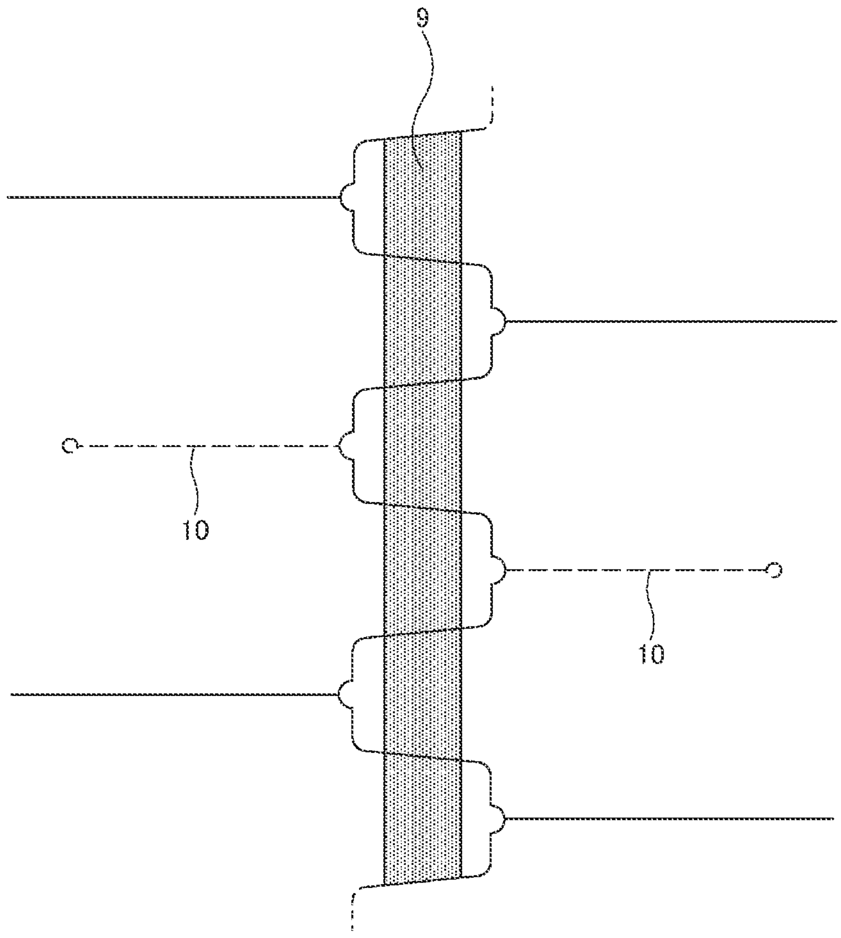

TAPE-TYPE DISPOSABLE DIAPER

CROSS-REFERENCE TO RELATED APPLICATIONS

This application is the U.S. national stage application of International Application PCT/JP2022/002763, filed Jan. 26, 2022, which international application was published on Sep. 9, 2022, as International Publication WO 2022/185790 in the Japanese language. The International Application claims priority of Japanese Patent Application No. 2021-033331, filed Mar. 3, 2021. The international application and Japanese application are both incorporated herein by reference, in entirety.

FIELD OF ART

The present invention relates to tape-type disposable diapers.

BACKGROUND ART

A common tape-type disposable diaper has a ventral section extending forward of the center of the front-back dimension of the diaper and a dorsal section extending backward of the center of the front-back dimension of the diaper, and the dorsal section has fastening projections projecting from the opposed lateral portions thereof. Upon fitting the diaper on a wearer's body, the fastening projections are pulled from the opposed sides of the waist over to the exterior surface of the ventral section, and fastened thereon.

Such tape-type disposable diapers are not only for use by babies and infants, but also for use in nursing care (adult use), and have problems of easy loosening around the waist and around the legs.

In view of this, a fastening projection is conventionally provided in an edge area closer to the waist and in an edge area closer to the round-leg area, on each lateral side of the dorsal section. The fastening projection closer to the waist and the fastening projection closer to the round-leg area are crossed on each side, and the fastening projections closer to the waist are pulled obliquely downward and fastened to tightly constrict the waist, while the fastening projections closer to the round-leg area are pulled obliquely upward and fastened to tightly constrict the legs, which is so-called cross fastening and recommended.

For allowing fitting of a tape-type disposable diaper in a similar fashion, there is also proposed to make a fastening panel dividable into upper and lower parts by means of a perforated line provided in the free end area of the fastening panel, so that the user may tear along the perforated line to form a pair of upper and lower fastening projection parts (Patent Publication 1).

Further, there is also known a bifurcated fastening panel, wherein an integral fastening panel is bifurcated in its free end area to form a pair of upper and lower fastening projection parts, and tab portions are provided for easy peeling (Patent Publication 2). These solutions commonly have a pair of upper and lower fastening projections.

However, since the perforated line for dividing the free end area of the fastening panel into upper and lower parts is not noticeable, an unaccustomed wearer may fasten the entire fastening panel together onto the exterior surface of the ventral section without dividing along the perforated line, and may not do the cross fastening. When a wearer wears the diaper without the cross fastening, inferior fitting may result, leakage may occur, and uncomfortableness may be felt.

PRIOR ART PUBLICATION

Patent Publication

Patent Publication 1: JP 6087081 B
Patent Publication 2: JP 6440471 B

SUMMARY OF THE INVENTION

Problems to be Solved by the Invention

It is therefore a primary object of the present invention to make the perforated lines in the fastening tapes noticeable by the wearer.

Means for Solving the Problem

The tape-type disposable diapers which solve the above-mentioned problem are as follows:

<First Aspect>

A tape-type disposable diaper including:

- a crotch section containing a middle of a front-back direction of the diaper;
- ventral and dorsal regions extending forward and backward, respectively, of the middle of the front-back direction; and
- a fastening tape extending in a width direction of the diaper from each of opposed lateral portions of the dorsal region,
- wherein each fastening tape has a waist-side flap and a round-leg-side flap,
- wherein the waist-side flap and the round-leg-side flap have a proximal portion integrated via a perforated line extending in the width direction, and distal portions spaced from each other in the front-back direction,
- wherein the distal portion of the waist-side flap and the distal portion of the round-leg-side flap each have a fastening part provided with a hook member or an adhesive layer detachably fastenable to the ventral region,
- wherein, assuming that a part of a side edge of each fastening tape located between the fastening part of the waist-side flap and the fastening part of the round-leg-side flap is equally divided in a front-back direction into a first edge located closer to a waist, a second edge located closer to a round-leg area, and a third edge located therebetween, at least part of the third edge is provided with a notch dented proximally from the first and second edges, and
- wherein an initial point of the perforated line is positioned on a proximal-most side of the notch.

<Effect>

The fastening tapes of the tape-type disposable diaper according to the present aspect respectively have a local notch provided in its side edge between the fastening part of the waist-side flap and the fastening part of the round-leg-side flap, so that the user is likely to find this notch visually, and also recognize the perforated line extending in the width direction from the notch. Further, with the initial point of the perforated line positioned on the proximal-most side of the notch, upon tearing from the notch as the starting point, the force for tearing along the perforated line is easily focused on the notch to facilitate initiation of the tearing.

<Second Aspect>

The tape-type disposable diaper according to the first aspect, wherein each fastening tape is folded along a folding line extending in the front-back direction and passing between each fastening part and the notch, so that portions distal to the folding line are folded onto a portion proximal to the folding line, and fastened thereto by means of the fastening parts.

<Effect>

It is conventionally known to fold the fastening tapes for making the product compact. This aspect is characterized in the arrangement of the folding line to pass between each fastening part and the notch. In this way, with the fastening tapes folded down, most of the surroundings on the waist side and the round-leg side of the notch form a straight line extending in the front-back direction, whereas the notch is present therebetween, which makes the notch particularly noticeable. Further, with the fastening tape folded down, the notch and the perforated line being noticeable leads to tearing of the fastening tape in the folded state along the perforated line. For example, when the fastening parts are hook members, the fastening tape may be torn along perforated line without the hook members being touched, which is advantageous in that the skin surface of the user is hard to be hurt with the hook members.

<Third Aspect>

The tape-type disposable diaper according to the first or second aspect, wherein an angle of a contour of the notch with respect to the width direction at the initial point of the perforated line is 20 to 50 degrees.

<Effect>

When the contour of the notch is at an acute angle, specifically at 20 to 50 degrees, with respect to the width direction at the initial point of the perforated line, which is the starting point of the tearing, the force for tearing along the perforated line is more easily focused on the initial point of the perforated line, and initiation of the tearing may be facilitated. Note that the "angle" mentioned above means, when the notch has a curved contour, the angle of the tangent line to the curved contour with respect to the width direction at the initial point of the perforated line.

<Fourth Aspect>

The tape-type disposable diaper according to any one of the first to third aspects, wherein each fastening tape is symmetrical with respect to a virtual line extending in the width direction passing a center of a dimension in the front-back direction of the fastening tape, wherein the waist-side flap and the round-leg-side flap are each symmetrical with respect to a virtual line extending in the width direction passing a center of a dimension in the front-back direction, wherein each fastening part extends continuously in the front-back direction in a predetermined width along a predetermined position in a middle of the width direction of the distal portion, wherein each distal portion has a tab part located distally from and exclusive of the fastening part, and wherein a contour of a part of the side edge of the fastening tape located between the fastening part of the waist-side flap and the fastening part of the round-leg-side flap is such that a spaced distance in the front-back direction between the waist-side flap and the round-leg-side flap is longer in a middle area of a width direction than in an area on each side of the middle area in the width direction.

<Effect>

For the manufacture of fastening tapes, it is widely practiced to produce right and left fastening tapes without generation of waste materials, by adhering one continuous strip of hook members or continuously applying an adhesive in a predetermined width, to a substrate, such as nonwoven fabric, down the middle of the width of the substrate; dividing the resulting substrate into two in the width direction along a wave-like line corresponding to the side edges of the fastening tapes; and cutting the substrate at intervals corresponding to the dimension of each fastening tape in the direction of flow (sometimes referred to as trimless process hereinbelow). When the notch discussed above is formed through the application of the trimless process, depending on the contour of the part of the side edge of the fastening tape located between the fastening part of the waist-side flap and the fastening part 5*c* of the round-leg-side flap, the dimensions of the tab part could be too small to pinch easily. However, with the contour according to the present aspect, the dimensions of the tab part may be made larger to facilitate pinching thereof.

<Fifth Aspect>

The tape-type disposable diaper according to any one of the first to third aspects, wherein each fastening tape is symmetrical with respect to a virtual line extending in the width direction passing a center of a dimension in the front-back direction of the fastening tape, wherein the waist-side flap and the round-leg-side flap are each symmetrical with respect to a virtual line extending in the width direction passing a center of a dimension in the front-back direction, wherein each fastening part extends continuously in the front-back direction in a predetermined width along a predetermined position in a middle of the width direction of the distal portion, wherein each distal portion has a tab part located distally from and exclusive of the fastening part, and wherein a contour of a part of the side edge of the fastening tape located between the fastening part of the waist-side flap and the fastening part of the round-leg-side flap is composed of at least one of straight lines and curved lines having a radius of curvature of 30 or larger.

<Effect>

The fastening tapes according to this aspect may be manufactured easily. Further, by manufacturing the fastening tapes according to this aspect through the trimless process as discussed above, the tab parts could be smaller and harder to pinch, but are harder to be turned up while the diaper is worn, which is less likely to cause the tab parts being impeditive or accidental peeling of the fastening parts.

Effect of the Invention

According to the present invention, advantages are provided, such as noticeability of the perforated lines in the fastening tapes by the user.

BRIEF DESCRIPTION OF THE DRAWINGS

FIG. 1 is a plan view of a tape-type disposable diaper in its spread state, illustrating the interior surface thereof.

FIG. 2 is a plan view of the tape-type disposable diaper in its spread state, illustrating the exterior surface thereof.

FIG. 3 is a cross-sectional view taken along lines iii-iii in FIG. 1.

FIG. 4 is a cross-sectional view taken along lines iv-iv in FIG. 1.

FIG. 5 is a perspective view of the diaper in a worn state.

FIG. 6 is a plan view of a fastening tape.

FIG. 7(*a*) is a plan view of the fastening tape, and FIG. 7(*b*) is a plan view of the fastening tape in a folded state.

FIG. 8 shows a plan view of a fastening tape and an enlarged view of and around a notch.

FIG. 9 shows a plan view of a fastening tape and an enlarged view of and around notch.

FIG. 10 is a plan view of a fastening tape.

FIG. 11 is a plan view of a fastening tape.

FIG. 12 illustrates manufacture of the fastening tapes.

EMBODIMENTS FOR CARRYING OUT THE INVENTION

An embodiment of the present invention will now be discussed in detail with reference to the attached drawings.

FIGS. 1 to 4 show an example of a tape-type disposable diaper which has a crotch section C containing the middle of the front-back direction LD of the diaper, and a ventral region F and a dorsal region B extending forward and backward, respectively, of the middle of the front-back direction of the crotch section C, and has a fastening tape 5 extending in the width direction WD from each of the opposed lateral portions of the dorsal region B. This disposable diaper has a basic structure including a liquid-impervious sheet 1, a liquid-pervious top sheet 2, and an absorbent body 3 interposed between the inner surface of the liquid-impervious sheet 1 and the liquid-pervious top sheet 2.

<Absorbent Body>

The absorbent body 3 may be an accumulation of pulp fibers, an assembly of filaments, such as of cellulose acetate, or nonwoven fabric, to which a high-absorbent polymer may be mixed, fixed, or otherwise, as required. The absorbent body 3 may be wrapped with crepe paper (not shown), where necessary. The shape of the absorbent body 3 may be an hourglass shape as in the illustrated embodiment, rectangular shape, or the like, and may suitably be decided. The absorbent body 3 may preferably have a pulp basis weight of about 100 to 500 g/m$^2$, and a thickness of about 1 to 15 mm. The basis weight of the high-absorbent polymer may preferably be about 0 to 300 g/m$^2$.

<Liquid-Impervious Sheet>

The liquid-impervious sheet 1 extends outwards beyond the circumference of the absorbent body 3, and blocks migration of the bodily waste absorbed in the absorbent body 3 down to the underside thereof. The liquid-impervious sheet 1 may be a plastic film, such as a polyethylene film, and a sheet having moisture-permeability without impairing water-shielding property may be used for preventing dampness. Such a water-shielding, moisture-permeable sheet may be a microporous sheet obtained by kneading an inorganic filler in a polyolefin-based resin, such as polyethylene or polypropylene, in a molten state, forming the resulting mixture into a sheet, and then uni- or biaxially drawing the sheet. The liquid-impervious sheet 1 has a weight per unit area of preferably 13 to 40 g/m$^2$, and a thickness of 0.01 to 0.1 mm.

In order to impart fabric-like appearance and texture to the exterior surface of the diaper, the liquid-impervious sheet 1 is covered with an exterior sheet 12 over its under face, and the outer edges of the sheets 1 and 12 extend up to the outer edge of the diaper. The exterior sheet 12 may be formed of various nonwoven fabric, and may preferably be spunbonded nonwoven fabric. The exterior sheet 12 may be omitted.

<Side Barrier Sheet>

As shown in FIGS. 3 and 4, to each of the opposed lateral portions on the interior surface of the article (in the illustrated embodiment, from each of the side edge portions of the top face of the top sheet 2 to the top face of the liquid-impervious sheet 1 extending laterally thereto), a side barrier sheet 4 is adhered in its outer portion 4*x* in the width direction all over the front-back direction. The side barrier sheet 4 may be formed of various nonwoven fabric (preferably spunbonded nonwoven fabric), plastic films similar to those used for the liquid-impervious sheet, or a laminate of these in the form of a sheet. In view of the touch on the skin, nonwoven fabric subjected to water-repellent treatment is preferred. The portion 4*c* of the side barrier sheet 4 closer to the center of the width direction of the diaper is fixed to the interior surface of the article (in the illustrated embodiment, the top face of the top sheet 2) in both end areas in the front-back direction by means of a hot melt adhesive or the like, while the middle area between the end areas is a non-fixed free portion 4*f*. In the free edge area of this free portion 4*f* (the edge area closer to the center of the width direction in the spread state), elongate elastic members 4G are fixed in a state of stretching in the front-back direction LD with a hot melt adhesive or the like. A plurality of such elongate elastic members 4G are disposed at predetermined intervals in the illustrated embodiment, but only one of such elastic members 4G may be disposed. The elongate elastic members 4G (or other elongate elastic members) may be made of a material that is usually used, such as natural rubber or synthetic rubber formed into strings, threads, ribbons, or the like shape, specifically, for example, polystyrene rubber, polyolefin rubber, polyurethane rubber, polyester rubber, polyurethane, polyethylene, polystyrene, styrene-butadiene copolymers, silicone, or polyester. The free portion 4*f*, under the contracting force of the elongate elastic members 4G, forms a side barrier which stands up with respect to the interior face of the article (in the illustrated embodiment, the top face of the top sheet 2) as shown in FIG. 4. The root 4*b* of this standup portion is located at the boundary between the fixed outer portion 4*x* in the width direction and the inner portion 4*c* of the side barrier sheet 4. Note that the areas hatched with positive slope in FIG. 1 represent the fixed portions of the side barrier sheet 4. The disposable diaper 100 is provided in the front-back direction LD with round-leg elastic members 14 extending along each of the opposed side edges (the portion to be the edge of each leg opening) Le, with the elastic members stretched in the direction of extension. With the round-leg elastic members 14 extending along each of the opposed side edges Le, the opposed side edges Le are pressed against the circumference of the legs of the wearer to hardly cause leaking through the round-leg areas, which is preferred. The number of the round-leg elastic members 14 on each of the right and left sides may suitably be decided.

<Flaps or the Like>

In the end areas of the disposable diaper 100 opposed in the front-back direction, the liquid-impervious sheet 1, the exterior sheet 12, the top sheet 2, and the side barrier sheets 4 extend forward and backward beyond the front and back ends of the absorber body 3 to form end flaps EF exclusive of the absorber body 3. On the other hand, in the opposed right and left side areas of the disposable diaper 100, the liquid-impervious sheet 1, the exterior sheet 12, the top sheet 2, and the side barrier sheets 4 extend laterally beyond the opposed side edges of the absorber body 3 to form side flaps exclusive of the absorber body 3. Portions of the side flaps in the ventral region F closer to the waist and portions of the side flaps in the dorsal region B closer to the waist extend laterally outward compared to the middle portion therebetween, and are referred to as waist-side side flaps SF, which form the waist zone of the diaper.

On the other hand, the disposable diaper 100 has in the front-back direction LD, a crotch section C wherein the opposed side edges (portions to be the edges of the leg openings) curved along the surface of the legs of the wearer define a centrally narrowed area, and ventral waist section TF and dorsal waist section TB extending forward and backward, respectively, of the crotch section C and having the opposed side edges extending straight along the front-back direction LD.

The dorsal waist section TB has a fastening tape 5 attached extending from each of the opposed side edges thereof, while the ventral waist section TF has a target tape 6 attached on its surface along the width direction WD. Each fastening tape 5 has a fixed zone 5*f* fixed among the sheets in the dorsal waist section TB by means of a hot melt adhesive or the like, and a main zone 5*e* extending outwards in the width direction from among the sheets at the side edge of the dorsal waist section TB, and is dividable into a waist-side flap 51 and the round-leg-side flap 52 by tearing along a perforated line 10 provided in the main zone 5*e* in the middle of the front-back direction. The waist-side flap 51 and the round-leg-side flap 52 have a proximal portion 5*g* integrated via the perforated line 10, and distal portions 5*h* spaced apart from each other in the front-back direction LD. In the vicinity of the proximal end of the perforated line 10 in the fastening tape 5, a C-shaped notch may be provided for dissipating the momentum of tearing of the perforated line 10, in order to avoid further tearing inwards in the width direction beyond the proximal end.

Nonwoven fabric of sufficient strength, in particular, a sheet having a plurality of stacked layers of nonwoven fabric or polyethylene-laminated nonwoven fabric may preferably be used as a substrate 8 of the fastening tapes 5.

Each of the waist-side flap 51 and the round-leg-side flap 52 is provided on its interior surface with a fastening part 5*c* having a hook member 9 detachably fastenable to the exterior surface of the ventral region F. In the illustrated embodiment, only one fastening part 5*c* is provided in each of the distal portions 5*h* of the waist-side flap 51 and the round-leg-side flap 52, but a plurality of them may be provided at a plurality of locations at intervals in the width direction WD. The hook member 9 may preferably be a male part of a mechanical fastener (hook and loop fastener), where the hooks of the mechanical fastener detachably engage the loops of the target tape 6. When the exterior sheet 12 is nonwoven fabric, the fibers of the nonwoven fabric function as the loops, so that the target tape 6 may be omitted. The fastening parts 5*c* may be a pressure-sensitive adhesive layer, where the target tape 6 may preferably be a resin tape (sheet) having a smooth surface.

As shown in FIG. 6, the waist-side flap 51 and the round-leg-side flap 52 may have a stretchable area wherein the main zone 5*e* elastically stretches/contracts in the width direction WD. Means for constituting the stretchable area are not particularly limited, and the fastening projections may be formed of a material which is elastically stretchable/contractible per se, such as stretchable nonwoven fabric or rubber sheet. In the illustrated embodiment, at least part of the width WD of the main zone 5*e* of each flap 51, 52 is formed of a first sheet and a second sheet adhered together, between which elastic members 20 are fixed to make the part stretchable. The elastic members 20 may be not only in an elongate form, but also be in a sheet form.

<Notch>

As shown in FIG. 7(*a*), assuming that the part of the side edge of the fastening tape 5 located between the fastening part 5*c* of the waist-side flap 51 and the fastening part 5*c* of the round-leg-side flap 52 is equally divided into three subparts in the front-back direction LD, and the subpart located closer to the waist is referred to as a first edge 21, the subpart located closer to the round-leg area is referred to as a second edge 22, and the subpart located therebetween is referred to as a third edge 23, it is preferred to provide at least part of the third edge 23 with a notch 11 dented proximally from the first and second edges 21 and 22, and a perforated line 10 extending from the proximal-most side of the notch 11 toward the middle of the width direction of the diaper, so that the notch 11 preferably causes the user to notice the perforated line 10 upon fitting the diaper. When the user finds the perforated line 10 and tears along the same, the divided fastening tape 5 is separated into the waist-side-flap 51 and the round-leg-side flap 52 to allow them to be cross-fastened as shown in FIG. 5. With the initial point of the perforated line 10 positioned on the proximal-most side of the notch 11, upon tearing from the notch 11 as the starting point, the force for tearing along the perforated line 10 is easily focused on the notch 11 to facilitate initiation of the tearing.

In the product state as shown in FIG. 7(*b*), it is preferred that the waist-side flap 51 and the round-leg-side flap 52 are folded along the folding line 7 extending in the front-back direction LD between the fastening parts 5*c* and the notch 11, onto the proximal portion 5*g* of the fastening tape 5 and fastened thereto by means of the hook members 9. In this way, with the fastening tape 5 folded down, most of the surroundings on the waist side and the round-leg side of the notch 11 form a straight line extending in the front-back direction LD, whereas the notch 11 is present therebetween, which makes the notch 11 particularly noticeable. Further, with the fastening tape 5 folded down, the notch 11 and the perforated line 10 are noticeable, which leads to tearing of the fastening tape 5 in the folded state along the perforated line 10. For example, when the fastening parts 5*c* are hook members 9, the perforated line 10 may be torn without the hook members 9 being touched, which is advantageous in that the skin surface of the user is hard to be hurt with the hook members 9.

Referring to FIG. 8, when the angle $\alpha$ of the contour of the notch 11 with respect to the width direction WD at the tip of the notch 11 is acute, the force for tearing along the perforated line 10 is easily focused on the proximal-most side of the notch 11 and, specifically at 20 to 50 degrees, initiation of the tearing along the perforated line 10 may be facilitated. When the notch 11 has a curved contour as shown in FIG. 9, the angle of the tangent line of the curve with respect to the width direction WD is taken as the angle $\alpha$. The shape and dimensions of the notch 11 are not particularly limited, and the dimension (maximum) 11L in the front-back direction LD of the notch 11 is preferably 15 mm to 25 mm, and the dimension (maximum) 11W in the width direction WD of the notch 11 is preferably 5 mm to 15 mm. Note that the notch 11 provided in at least part of the third edge 23, as is clear from the fact that it is dented proximally from the first and second edges 21 and 22, refers only to the extent of the third edge 23. That is, even if the notch appears to be continuous from the first edge 21 over to the second edge 22 as in the embodiments shown in FIGS. 8 to 11, the notch 11 according to the present invention is only the part positioned in the extent of the third edge 23, and thus the dimensions of the notch 11 are as illustrated.

As shown in FIGS. 7 to 9 and 11, the contour of the part of the side edge of the fastening tape 5 located between the fastening part 5*c* of the waist-side flap 51 and the fastening part 5*c* of the round-leg-side flap 52 may be such that the spaced distance in the front-back direction LD between the flaps 51 and 52 is not increasing but decreasing toward the initial point of the perforated line, or such that the spaced distance in the front-back direction LD is partly increasing.

The shape of the fastening tape 5 is preferably symmetrical with respect to the virtual line extending in the width direction WD passing the center of the front-back direction of the fastening tape 5, as in the illustrated embodiments. In this case, the waist-side flap 51 and the round-leg-side flap 52 are in the same shape, and part of the virtual line between the waist-side flap 51 and the wound-leg-side flap 52 and the perforated line 10 are at the same position. Further, it is preferred that the waist-side flap 51 is also symmetrical with respect to the virtual line extending in the width direction WD passing the center of the front-back direction thereof, and so is the round-leg-side flap 52. Such fastening tapes 5 may be manufactured, as shown in FIG. 12, by adhering hook members 9 in the form of a continuous strip or applying an adhesive in a predetermined width, on a substrate 8, such as nonwoven fabric, down the middle of the width of the substrate 8; dividing the resulting substrate into two in the width direction WD along a wave-like line corresponding to the side edges of the fastening tapes 5; and cutting the substrate in the direction of flow at intervals corresponding to the dimension in the front-back direction LD of each fastening tape 5 (trimless process).

<Tab Part>

It is preferred that a part of the distal portion 5*h* of each of the waist-side flap 51 and the round-leg-side flap 52 located distally from the fastening part 5*c* and exclusive of the fastening part 5*c* is left as a tab part 13.

The shape and dimensions of the tab part 13 is not particularly limited, and it is preferred that the dimension 13L (maximum, if varies) in the front-back direction LD of the tab part 13 is 10 to 20 mm, and the dimension 13W (maximum, if varies) in the width direction WD of the tab part 13 is 15 mm to 25 mm. A larger tab part 13 may be more easily pinched and cause the notch 11 to be more noticeable but, in the absence of the fastening part 5*c*, the tab part 13 may tend to be raised and turned up in use. On the other hand, a smaller tab part 13 may be harder to be pinched and cause the notch 11 to be less noticeable, but the tab part 13 may be harder to be raised and turned up. In particular, when the notch 11 is formed through the trimless process mentioned above, the part of the side edge of the fastening tape 5 located between the fastening part 5*c* of the waist-side flap 51 and the fastening part 5*c* of the round-leg-side flap 52 forms the contour of the tab part 13, depending on which the tab part 13 may be smaller in dimensions and harder to pinch or, conversely, easier to turn up. For example, as shown in FIG. 10, when the contour of the part of the side edge of the fastening tape 5 located between the fastening part 5*c* of the waist-side flap 51 and the fastening part 5*c* of the round-leg-side flap 52 is such that the spaced distance 11L in the front-back direction between the flaps 51 and 52 is longer in the middle area of the width direction WD than in the areas on both sides of the middle area in the width direction WD (for example, 1.2 to 1.5 times the maximum spaced distance in the front-back direction LD between the flaps 51 and 52 on the contour of the part of the side edge located between the fastening part 5*c* of the waist-side flap 51 and the fastening part 5*c* of the round-leg-side flap 52), the resulting tab part 13 may be easier to be pinched, but may be more likely to be raised or turned up in use. In contrast, as shown in FIG. 11, when the contour of at least the part (preferably all) of the side edge of the fastening tape 5 located between the fastening part 5*c* of the waist-side flap 51 and the fastening part 5*c* of the round-leg-side flap 52 is composed only of at least one of straight lines and curved lines having the radius of curvature of 30 or larger, the tab part is smaller and harder to be manipulated upon fitting of the diaper, but may be harder to be raised or turned up when the diaper is worn. Further, the division along the wave-like line in the production of the fastening tapes 5 is facilitated, which enhances production stability.

INDUSTRIAL APPLICABILITY

The present invention is applicable to tape-type disposable diapers as in the embodiments discussed above.

DESCRIPTION OF REFERENCE NUMERALS

1: liquid-impervious sheet
2: top sheet
3: absorbent body
4: side barrier sheet
5: fastening tape
5*c*: fastening part
5*e*: main zone
5*f*: fixed zone
5*g*: proximal portion
5*h*: distal portion
51: waist-side flap
52: round-leg-side flap
6: target tape
7: folding line
8: substrate
9: hook member
10: perforated line
11: notch
11L: dimension in front-back direction of notch 11
11W: dimension in width direction of notch 11
12: exterior sheet
13: tab part
13L: dimension in front-back direction of tab part 13
13W: dimension in width direction of tab part 13
14: round-leg elastic member
20: elastic member
21: first edge
22: second edge
23: third edge
F: ventral region
B: dorsal region
100: disposable diaper

The invention claimed is:

1. A tape-type disposable diaper comprising:

a crotch section containing a middle of a front-back direction of the diaper;

ventral and dorsal regions extending forward and backward, respectively, of the middle of the front-back direction; and a fastening tape extending in a width direction of the diaper from each of opposed lateral portions of the dorsal region, wherein each fastening tape has a waist-side flap and a round-leg-side flap, wherein the waist-side flap and the round-leg-side flap have a proximal portion integrated via a perforated line extending in the width direction and passing a center of a dimension in the front-back direction of the fastening tape, and distal portions spaced from each other in the front-back direction, wherein the distal portion of the waist-side flap and the distal portion of the round-leg-side flap each have a fastening part provided with a hook member or an adhesive layer detachably fastenable to the ventral region, wherein a shape of each fastening tape is symmetrical with respect to the perforated line, wherein a shape of the waist-side flap and a shape of the round-leg-side flap are each symmetrical with respect to a virtual line extending in the width direction passing a center of a dimension in the front-back direction, wherein each fastening part extends continuously in the front-back direction in a predetermined width along a predetermined position in a middle of the width direction of the distal portion, wherein each distal portion has a tab part located distally from and exclusive of the fastening part, wherein a contour of a part of a side edge of the fastening tape located between the fastening part of the waist-side flap and the fastening part of the round-leg-side flap is a contour of an edge of the tab part, wherein, a part of a side edge of each fastening tape located between the fastening part of the waist-side flap and the fastening part of the round-leg-side flap is equally divided among three in the front-back direction, wherein the three are defined as a first edge located closer to a waist, a second edge located closer to a round-leg area, and a third edge located between the first edge and the second edge, at least part of the third edge being provided with a notch dented proximally from the first and second edges, wherein an initial point of the perforated line is positioned on a proximal-most side of the notch, wherein an edge of a part located between the fastening part of the waist-side flap and the fastening part of the round-leg-side flap has a first straight line part extending linearly from a base point of a back side of the notch toward the back side and a second straight line part extending linearly from a base point of a front side of the notch toward the front side, and wherein an entire edge of the notch has a curved contour without any inflection points.

2. The tape-type disposable diaper according to claim 1, wherein each fastening tape is folded along a folding line extending linearly in the front-back direction and passing between each fastening part and the first and second straight line parts, so that portions distal to the folding line are folded onto a portion proximal to the folding line, and fastened thereto by means of the fastening parts.

3. The tape-type disposable diaper according to claim 2, wherein the waist-side flap and the round-leg-side flap have a stretchable area provided from the distal portion to the proximal portion, wherein the stretchable area is configured to elastically stretch and contract in the width direction, and wherein the stretchable area is formed of a first sheet and a second sheet adhered together, and elastic members are fixed between the first sheet and the second sheet.

4. The tape-type disposable diaper according to claim 1, wherein an edge of the notch has a half-circle contour.

* * * * *